Figure 1:
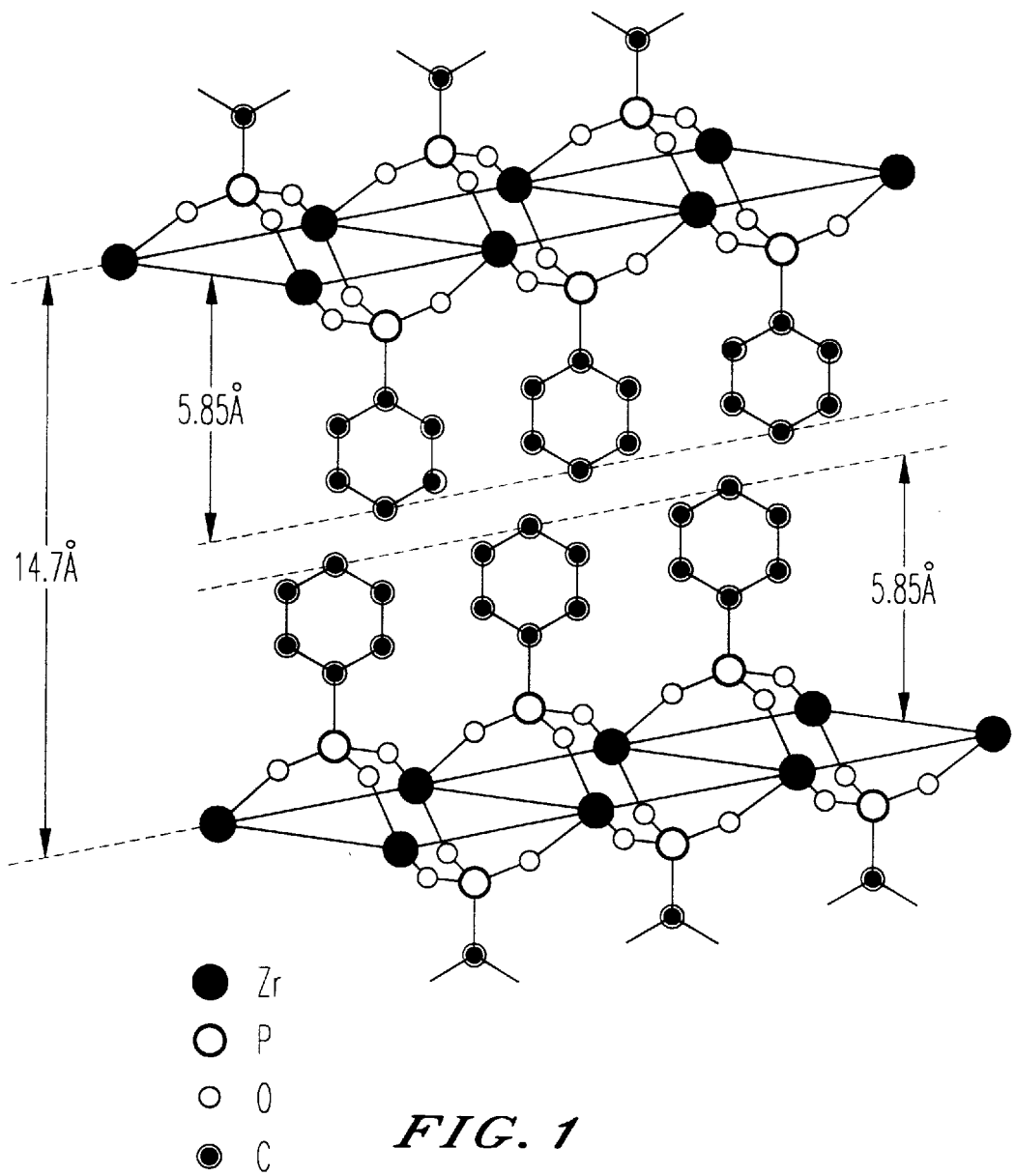

US005892080A

United States Patent [19]
Alberti et al.

[11] Patent Number: 5,892,080
[45] Date of Patent: Apr. 6, 1999

[54] MESOPOROUS CRYSTALLINE ACID COMPOSITION OF A DIPHOSPHONATE-PHOSPHITE OF A TETRAVALENT METAL WHICH CAN BE USED AS A CATALYST

[75] Inventors: Giulio Alberti, Perugia; Riccardo Vivani, Citta' Della Pieve; Chiara Antonini Vitali; Piergiorgio Zapelli, both of Monterotondo, all of Italy

[73] Assignee: Eniricerche S.p.A., San Donato Milanese, Italy

[21] Appl. No.: 942,484

[22] Filed: Oct. 2, 1997

Related U.S. Application Data

[63] Continuation of Ser. No. 628,512, Apr. 5, 1996, abandoned.

[30] Foreign Application Priority Data

Apr. 7, 1995 [IT] Italy ................................. MI95A0710

[51] Int. Cl.⁶ ................ C07F 7/00; B01J 31/00
[52] U.S. Cl. ................ 556/19; 556/13; 556/51; 556/54; 502/162
[58] Field of Search ................ 556/13, 19, 51, 556/54; 502/162

[56] References Cited

U.S. PATENT DOCUMENTS 5,166,380  11/1992  Alberti et al. ............................. 556/19
5,290,746  3/1994  Alberti et al. ........................... 502/162

FOREIGN PATENT DOCUMENTS 0 492 694  7/1992  European Pat. Off. .

OTHER PUBLICATIONS

Chemical Abstracts, vol. 119, No. 22, Nov. 29, 1993, AN 240222S.
Angewandte Chemie, vol. 32, No. 9, Nov. 1993, Giulio Alberti, et al. "Zirconium Phosphite (3,3',5,5'—Tetramethyl–Biphenyl)Diphosphonate, A Microporous, Layered, Inorganic–Organic Polymer".

*Primary Examiner*—Porfirio Nazario-Gonzalez
*Attorney, Agent, or Firm*—Oblon, Spivak, McClelland, Maier & Neustadt, P.C.

[57] ABSTRACT

Solid mesoporous crystalline composition of diphosphonate-phosphite of a tetravalent metal, with a limited distribution of mesopores having the formula $$M[(O_3P\text{—}R\text{—}PO_3)_{1-x-y}(HPO_3)_{2x}(O_3P\text{—}R\text{—}PO_3H_2)_{2y}]$$

wherein: M is a tetravalent metal, R is a bivalent organic radical, x varies from 0.3 to 0.6, y varies from 0.05 to 0.3. The process for its production is described, together with its uses and a solid catalyst containing —SO$_3$H acid groups, active in the conversion processes of hydrocarbons, which can be obtained from said mesoporous crystalline composition by treatment with a sulfonicphosphonic or arylphosphonic acid, followed, only in the case of treatment with arylphosphonic acid, by sulfonation with a sulfonating agent.

26 Claims, 12 Drawing Sheets

MESOPOROUS CRYSTALLINE ACID COMPOSITION OF A DIPHOSPHONATE-PHOSPHITE OF A TETRAVALENT METAL WHICH CAN BE USED AS A CATALYST

This application is a Continuation of application Ser. No. 08/628,512, filed on Apr. 5, 1996, now abandoned.

The present invention relates to a solid mesoporous crystalline composition of diphosphonate-phosphite of a tetravalent metal, with a limited distribution of mesopores, the process for its production and its uses. The present invention also relates to a solid catalyst containing —$SO_3H$ acid groups which can be obtained from the above solid mesoporous crystalline composition, active in conversion processes of hydrocarbons.

G. Alberti, S. Allulli, U. Costantino and N. Torassini, in J. Inorg. Nucl. Chem., 40, 1113 (1978), described the production of lamellar compounds, with a structure similar to that of zirconium α-phosphate [α-Zr(HPO$_4$)$_2$.H$_2$O], for reactions between phosphonic acids and the salts of tetravalent metals. These lamellar phosphonates can be represented with the general formula M(RPO$_3$)$_2$, wherein M is a tetravalent metal and R is an organic radical. A specific example is zirconium benzene-phosphonate, whose structure is shown in FIG. 1.

After this basic discovery, a great deal of research was carried out in this field for the considerable applicative potentialities of the compounds obtained and in particular the following technical and patent literature can be mentioned: G. Alberti, U. Costantino and M. L. Luciani, J. Chromatog., 180, 45(1979); G. Alberti and U. Costantino, J. Mol. Catal., 27, 235(1984); G. Alberti, U. Costantino, J. Korney and M. L. Luciani, Reactive Polymers, 4, 1(1985); G. Alberti, U. Costantino and G.Perego, J. Solid State Chem., 63, 455(1986); EP 10.366; EP 10.857; M. B. Dines and P. M. Di Giacomo, Inorg. Chem. 20, 92(1981); P. M. Di Giacomo and M. B. Dines, Polyhedron, 1, 61(1982); M. B. Dines, P. M. Di Giacomo, K. P. Collahan, P. C. Griffith, R. H. Lane and R. E. Cooksey, A.C.S. Series 192, Chap 13, ACS, Washington D.C., 1982; M. B. Dines, R. E. Cooksey, P. C. Griffith and R. H. Lane, Inorg. Chem. 22, 1003 (1983); M. B. Dines and P. C. Griffith, Polyhedron 2 607(1983); C. Y. Ortiz-Avila and A. Clearfield, Inorg. Chem. 24, 1773 (1985); A. Clearfield, Design of New Materials, Plenum Press, New York (1987), pages 121–134; and A. Clearfield; Chem.Rev.88, 125(1988).

Figure 2:
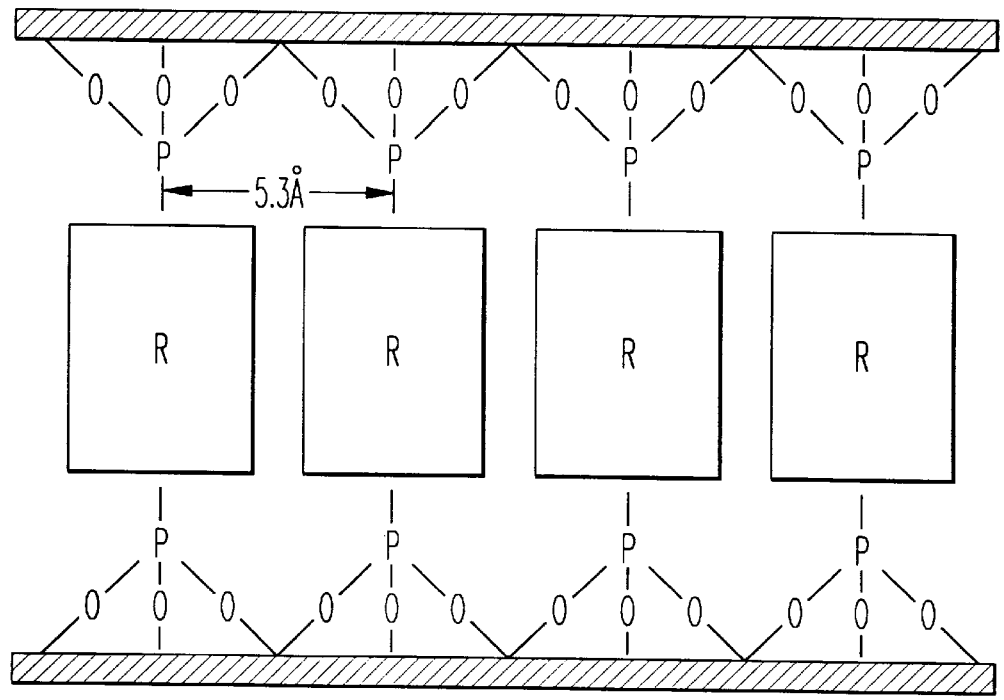
Figure 3:
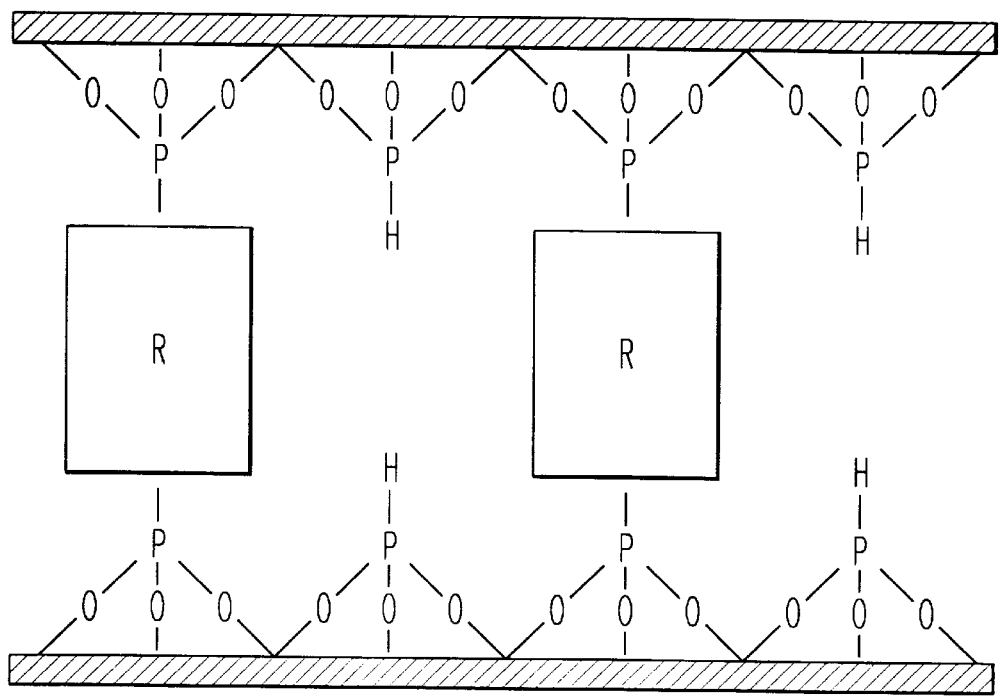

In EP 10.366 and EP 10.857 some compositions of the pillared type are described, obtained by reactions between salts of tetravalent metals and diphosphonic acids, with the formula M$^{IV}$[R(PO$_3$)$_2$], (wherein M is a tetravalent metal and R is a bivalent organic radical), whose structure is schematically shown in FIG. 2. Unfortunately, owing to the a structure of the layers, the distance between the central axes of the adjacent pillars is only 5.3 Å. Considering that the average Van der Waals diameter is about 4.4 Å for the pillars consisting of aliphatic chains and about 3.7 Å for the pillars consisting of aromatic rings, it can be deduced that the free intercolumn space is smaller than the diameter of the molecules and consequently the compositions obtained cannot be used as molecular sieves. To introduce a certain degree of microporosity between the layers a proposal was made to dilute the pillars by partially replacing them with very small groups of the R'—PO$_3$ type, for example H—PO$_3$, HO—PO$_3$ and CH$_3$—PO$_3$ (see for example Clearfield, mentioned above). The formation of a microcavity in an idealized composition, by the introduction of phosphite groups, is shown schematically in FIG. 3. In these compositions the dimensions of the cavity basically depend on the length of the pillar R(PO$_3$)$_2$ and the spacing between the pillars.

U.S. Pat. No. 5,166,380 subsequently described that it is possible to prepare a diphosphonate-phosphite of a tetravalent metal, in crystalline form, under such conditions that the HPO$_3$ groups, in addition to the possible formation of micropores in the interstratum region, also induce the formation of a mesoporosity, which cannot be attributed to the formation of cavities in the interstratum region, and which has a rather limited distribution with the majority of the pores being within the range of 20–30 Å. This material is prepared by the reaction between a diphosphonic acid, phosphorous acid and oxychloride of a tetravalent metal, operating in a solvent consisting of dimethylsulfoxide/water containing hydrofluoric acid.

We have now surprisingly found a new solid mesoporous crystalline composition of diphosphonate-phosphite of a tetravalent metal with a porosity within the range of mesopores, with at least 50% of the pores having a diameter greater than 30 Å and less than or equal to 50 Å.

In particular the composition of the present invention is a diphosphonate of a tetravalent metal containing acid phosphite groups and diphosphonate groups anchored to the surface, which can be defined with the general formula (I)

$$M[(O_3P—R—PO_3)_{1-x-y}(HPO_3)_{2x}(O_3P—R—PO_3H_2)_{2y}]$$

wherein: M is a tetravalent metal
R is a bivalent organic radical
x varies from 0.3 to 0.6
y varies from 0.05 to 0.3.
the composition being in the form of a crystalline solid having the following characteristics:
  lamellar structure of the a type with an interstratum distance of between 7.4 and 20 Å;
  B.E.T. surface area of between 250 and 400 m$^2$/g
  porosity in the range of mesopores, with at least 50% of the pores having a diameter greater than 30 Å and less than or equal to 50 Å.

In particular, in the above formula, M is a tetravalent metal which can be conveniently selected from zirconium, titanium and tin, and is preferably zirconium owing to the greater stability to hydrolysis of the relativeadso composition.

The bivalent organic radical R is conveniently a very short radical so that micropores will be formed in the interstratum region which are so small as to be inaccessible to common molecules. Alternatively non-rigid R radicals can be used, such as for example aliphatic chains which tend to occupy the spaces created by the HPO$_3$ groups with small dimensions, with a consequent decrease in the interstratum distance. In accordance with this R is selected from aliphatic bivalent organic radicals containing from 2 to 10 carbon atoms in the molecule, or aromatic radicals containing from 1 to 2 non-condensed rings, or from alkylaromatic radicals. Specific examples of R radical are: —CH$_2$CH$_2$—, —CH$_2$—(CH$_2$)$_2$—CH$_2$—, —CH$_2$—(CH$_2$)$_4$—CH$_2$—, —C$_6$H$_4$—, —C$_6$H$_4$—C$_6$H$_4$—, —CH$_2$—C$_6$H$_4$—CH$_2$—, —CH$_2$—C$_6$H$_4$—C$_6$H$_4$—CH$_2$—.

Preferred examples of the R radical are —C$_6$H$_4$— and —CH$_2$(CH$_2$)$_2$—CH$_2$—.

In the composition of the present invention the specific value of the interstratum distance depends on the R radical and, in relation to the particular R radical selected, the composition may or may not have a microporosity in the interstratum region. In addition, in the above formula the value of 2y refers to the quantity of acid diphosphonate groups present at the surface, and the specific value of y depends on the surface area.

More specifically, the composition of the present invention is a crystalline solid in which x varies from 0.3 to 0.6, and the groups present on the surface can either be phosphites themselves or diphosphonates. The latter differ from the internal ones as they have one of the phosphonic groups in acid form and their presence makes the total phosphorous/zirconium (or other tetravalent metal) ratio higher than 2, this being the typical value of lamellar compounds of the a type. The quantity of acid diphosphonate groups depends on the surface extension and can be determined by titrating the crystalline solid, dispersed in a solution of KCl (0.1–1M) with potassium hydroxide up to pH 7. The values of y vary from 0.05 to 0.3 depending on the surface extension. In addition the composition is a lamellar solid of the a type with an interstratum distance of between 7.4 and 20 Å or more, depending on the dimensions of the R radical, with a B.E.T. surface area of between 250 and 400 m$^2$/g, with a porosity within the range of mesopores and with at least 50% of the pores having a diameter greater than 30 Å and less than or equal to 50 Å. For example it is possible to have a porosity in the range of mesopores, with at least 50% of the pores with a diameter greater than 30 Å and less than 40 Å. The composition, depending on the R radical used, may or may not have a microporosity in the interstratum region.

The present invention also relates to a process for the preparation of the composition having formula (I) described above which comprises reacting a diphosphonic acid R(PO$_3$H$_2$)$_2$, phosphorous acid H$_3$PO$_3$, an oxychloride of a tetravalent metal MOCl$_2$, in a solvent selected from n-propanol or water containing hydrofluoric acid:

1—x—y (PO$_3$H$_2$)$_2$+2x H$_3$PO$_3$+MOCl$_2$→
M[(O$_3$P—R—PO$_3$)$_{1-x-y}$(HPO$_3$)$_{2x}$(O$_3$P—R—PO$_3$H$_2$)$_{2y}$]+2HCl+H$_2$O wherein R, M, x and y have the meaning defined above.

The process is carried out with a molar ratio between diphosphonic acid and phosphorous acid of between 1/2 and 1/20, with a molar ratio between hydrofluoric acid and tetravalent metal of between 5/1 and 30/1 and with a molar ratio between diphosphonic acid and tetravalent metal of between 0.5 and 2, at a temperature of between 10° and 130° C. and for a time of between 1 and 100 hours. The hydrofluoric acid is used as a concentrated aqueous solution.

Specific examples of diphosphonic acids R(P)$_3$H$_2$)$_2$ suitable for the purposes are: 1,4-benzene diphosphonic acid and 1,4-butane diphosphonic acid.

The preferred oxychloride of a tetravalent metal is selected from zirconyl chloride octahydrate ZrOCl$_2$.8H$_2$O and zirconyl chloride monohydrate ZrOCl$_2$.H$_2$O.

The reaction medium is important in the process of the present invention. In fact, a mixture of water/dimethylsulfoxide is described in the prior art (U.S. Pat. No. 5,166,380) as producing a porosity in the range of mesopores of between 20 and 30 Å, whereas if n-propylic alcohol or water are used, under suitable conditions, a porosity in the range of mesopores with at least 50% of the pores having a diameter greater than 30 Å and less than or equal to 50 Å, is surprisingly obtained.

At the end of the reaction the compound can be recovered from the reaction mixture by filtration or centrifugation, washed with the same solvent used for the synthesis and dried.

Owing to the limited distribution of mesopores in the region of 30–50 Å, the solid, crystalline compositions of the present invention are of great interest as molecular sieves for large molecules.

In these materials, in addition to the groups present on the surface, there can also be both diphosphonate and phosphite surface groups: the diphosphonate surface groups have a —PO$_3$H$_2$ acid group, not involved in the binding with the metal, which gives acid characteristics to the material useful in catalytic processes.

We have also found that it is possible to increase the surface acidity of these compounds obtaining materials with improved catalytic behaviour. In particular we have found that it is possible to exchange the diphosphonate and phosphite surface groups of these materials with phosphonic-sulfonic groups by topotactic exchange with a phosphonic-sulfonic acid. We have additionally found that the introduction of phosphonic-sulfonic groups can also be obtained by a preliminary topotactic exchange with arylphosphonic acid and the subsequent sulfonation of these groups with normal sulfonating agents.

A further object of the present invention therefore relates to a solid acid catalyst based on a diphosphonate-phosphite of a tetravalent metal which can be obtained with a process in which a diphosphonate-phosphite of a tetravalent metal, which can be defined with the following formula (I)

wherein: M is a tetravalent metal
R is a bivalent organic radical
x varies from 0.3 to 0.6
y varies from 0.05 to 0.3,
having a lamellar structure of the a type with an interstratum distance of between 7.4 and 20 Å, a B.E.T. surface area of between 250 and 400 m$^2$/g, porosity in the range of mesopores, with at least 50% of the pores having a diameter greater than 30 Å and less than or equal to 50 Å, is put in contact with a solution, in an aqueous and/or organic solvent, of:

a bifunctional phosphonic-sulfonic acid having general formula H$_2$O$_3$P—R'—SO$_2$X, wherein R' is a bivalent organic radical such as alkylene, arylene or a combination thereof, and X is a monovalent group such as OH or Cl; or an arylphosphonic acid containing one or more aromatic rings; for a time which is sufficient to at least partially exchange the diphosphonate and phosphite surface groups of the diphosphonate-phosphite of the tetravalent metal with phosphonic-sulfonic groups or respectively with arylphosphonic groups;

and, only in the case of the product exchanged with arylphosphonic acid, subjecting this solid to sulfonation with a sulfonating agent.

In formula (I) above, M preferably represents zirconium and R preferably represents a radical selected from those which can be defined with the formulae: —CH$_2$CH$_2$—, —CH$_2$—(CH$_2$)$_2$—CH$_2$—, —CH$_2$—(CH$_2$)$_4$—CH$_2$—, —C$_6$H$_4$—, —C$_6$H$_4$—C$_6$H$_4$—, —CH$_2$—C$_6$H$_4$—CH$_2$—, —CH$_2$—C$_6$H$_4$—C$_6$H$_4$—CH$_2$—. Preferred examples of the R radical are —C$_6$H$_4$— and —CH$_2$(CH$_2$)$_2$—CH$_2$—.

According to this aspect of the present invention the compound (I) is subjected to topotactic exchange with a bifunctional phosphonic-sulfonic acid or with an arylphosphonic acid. In the present invention, "topotactic exchange" means a reaction wherein a group (for example HPO$_3$) present in a solid compound is substituted by another group (for example Ar—PO$_3$) without the structure of the compound undergoing any particular variations.

As already indicated above, phosphonic-sulfonic acids which are suitable for the purpose are those which can be defined with the formula $H_2O_3P—R'—SO_2X$, wherein R' indicates a bivalent organic radical such as arylene, alkylene, or a combination thereof, and X indicates a monovalent group such as OH or Cl.

Examples of these phosphonic-sulfonic acids are phenylene-1-chlorosulfonyl-3-phosphonic acid and phenylenephosphonic-sulfonic acid.

Arylphosphonic acids which are suitable for the purpose are those in which the $—PO_3H_2$ group is bound directly or by other arylenic or alkylenic groups, to one or more phenylic groups, such as for example phenylphosphonic acid, biphenyl phosphonic acid, phenyl methyl phosphonic acid, diphenyl methylphosphonic acid, triphenyl methyl phosphonic acid. Phenylphosphonic acid is preferably used.

In the embodiment of this aspect of the present invention, a phosphonic-sulfonic acid or an arylphosphonic acid, selected from those indicated above, are dissolved in a solvent, at a concentration of between 0.01 and 2M and the solution thus obtained is put in contact with the solid compound (I), for the exchange of the surface groups.

The solvent used for this solution is water, or an organic solvent, or a mixed water/organic solvent, preferably dioxane for the use of chlorosulfonylphosphonic acid (X=Cl), dioxane/water at 90% in volume of dioxane for the use of phosphonic-sulfonic acid (X=OH), or water for the use of an arylphosphonic acid.

In particular, in the topotactic exchange reaction, the operating temperature generally varies from 20° to 100° C. and the contact time is between 1 and 72 hours. At the end of this period of time, the exchanged solid (I) is separated from the suspension, for example by filtration or centrifugation, washed with the same solvent used for the topotactic exchange reaction and dried.

When a chlorosulfonyl-phosphonic acid (X=Cl) is used, the exchanged solid must be briefly exposed to the air to enable the $—SO_2Cl$ groups present to be completely converted into $—SO_3H$ acid groups according to the reaction:
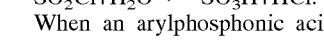

When an arylphosphonic acid is used, the product (I) exchanged is further subjected to sulfonation treatment with a sulfonating agent, in order to insert sulfonic groups onto the arylic portion introduced for the topotactic exchange. A sulfonating agent which is particularly suitable for the purpose is sulfuric anhydride, which can be conveniently used in the form of a solution in an inert solvent, such as sulfur dioxide. The sulfonation can be carried out at a temperature of between −30° and 50° C., for a time of between 10 minutes and 20 hours, operating in the presence of an excess of sulfonating agent. The exchanged and sulfonated product (I) is finally separated from the reaction mixture and subjected to purification treatment, for example by washing with an organic solvent such as tetrahydrofuran.

Owing to its acid characteristics, the catalyst can be used in reactions which require an acid catalysis, in particular in the conversions of hydrocarbons, such as for example alkylation, etherification, isomerization reactions.

The following experimental examples provide a better understanding of the present invention.

EXAMPLE 1
Preparation of mesoporous zirconium phenylenediphosphonate-phosphite 7.14 g of 1,4-phenylenediphoshonic acid and 11.48 g of phosphorous acid (reagent Carlo Erba RPE), are dissolved in 700 ml of n-propanol (Carlo Erba RPE), kept in a plastic container. 16.11 g of $ZrOCl_2.8H_2O$ (Merck, proanalysis) dissolved in 34.5 ml of concentrated HF (50% by weight, Carlo Erba RPE) and 65.5 ml of n-propanol are added to the limpid solution, maintained at 80° C. The solution thus obtained has the following composition: $[C_6H_4(PO_3H_2)_2]$= 0.038M, $[H_3PO_3]$=0.175M, $[Zr^{IV}]$=0.063M, $[HF]$=1.25M. The solution is maintained at 80° C. for 8 hours, ensuring that the volume remains constant. After this period the microcrystalline solid formed is separated from the solution by centrifugation, washed three times with about 500 ml of n-propanol and finally dried in an oven at 60° C. The solid zirconium diphosphonate-phosphite thus obtained is kept in a vacuum drier containing phosphoric anhydride.

Figure 4:
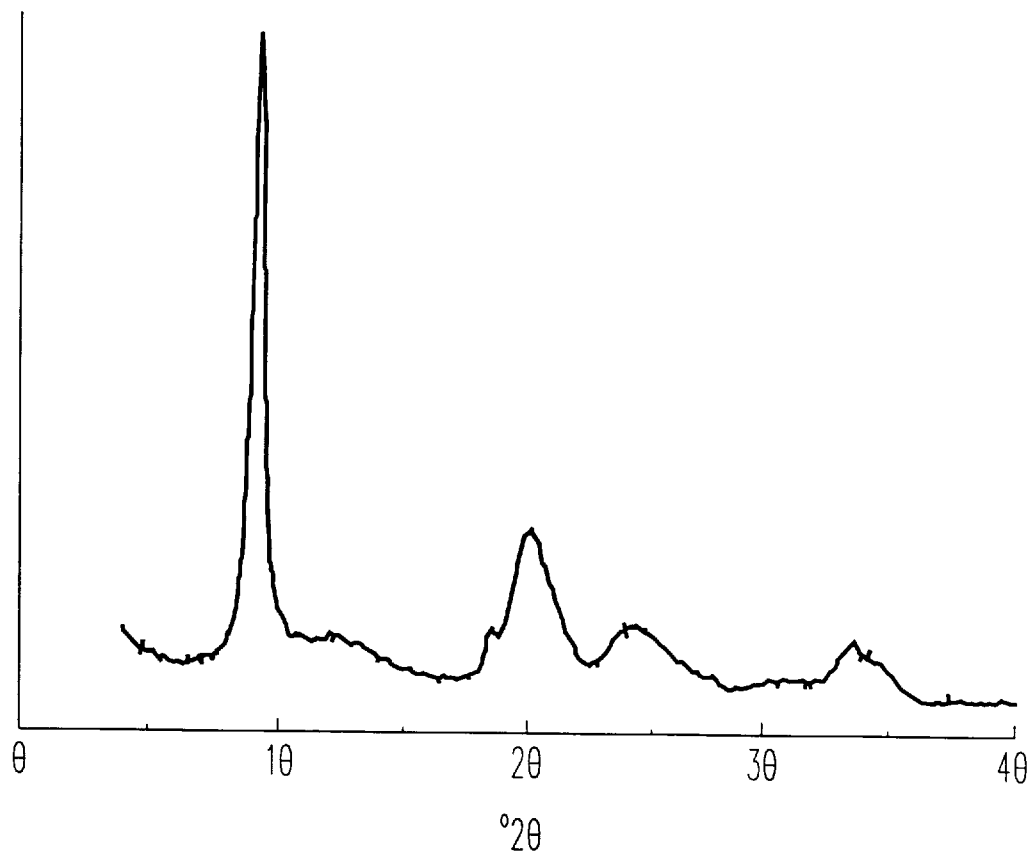
Figure 5:
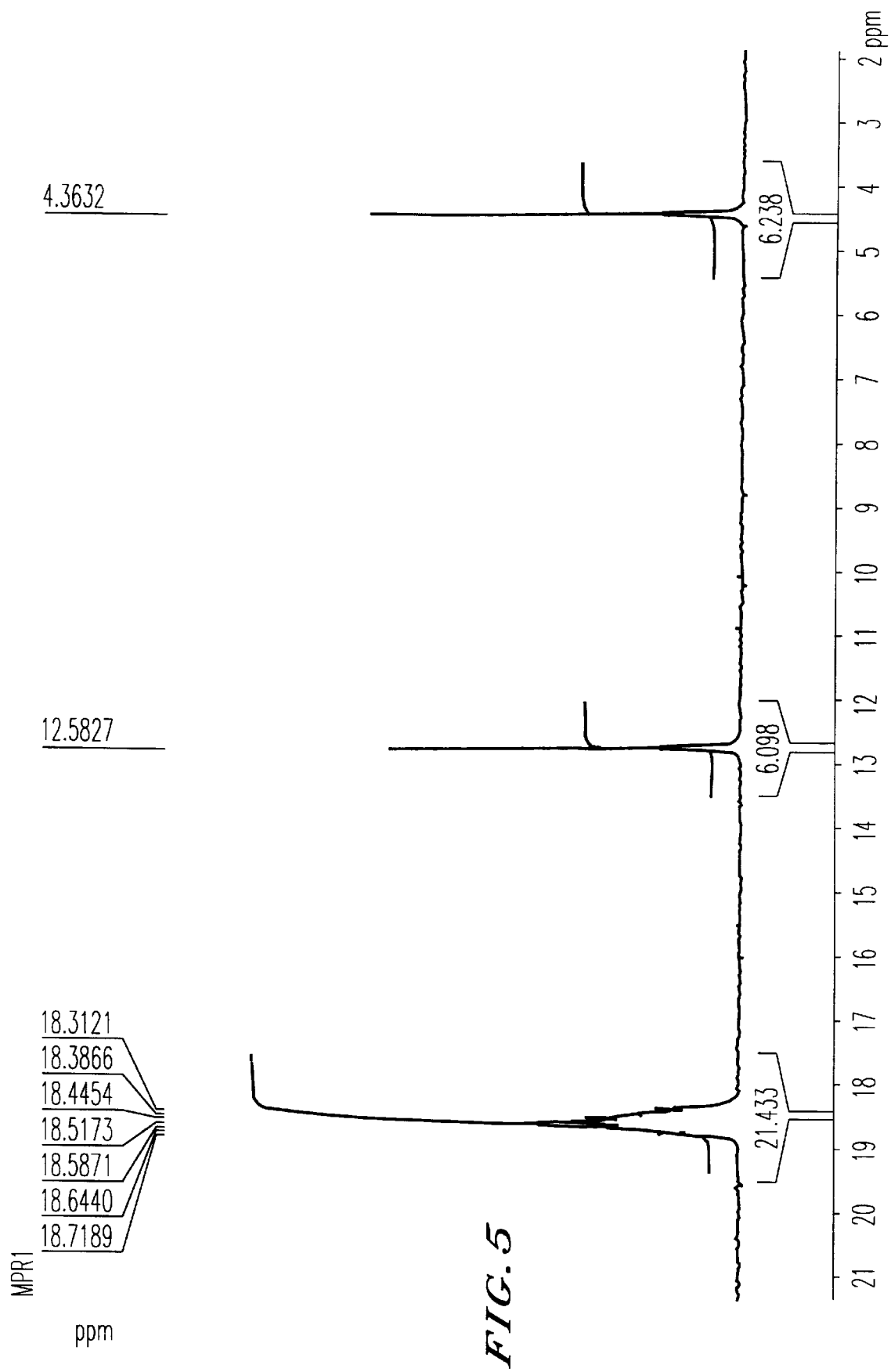
Figure 6:
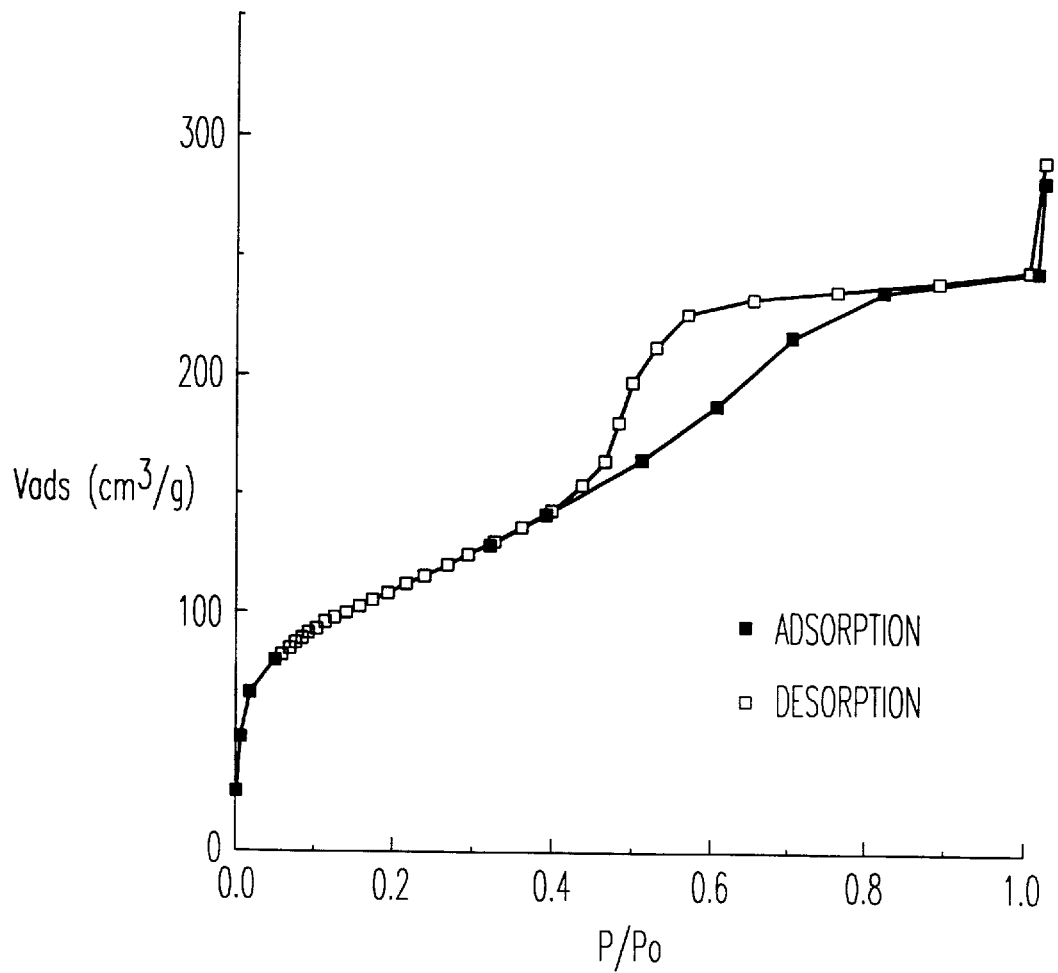
Figure 7:
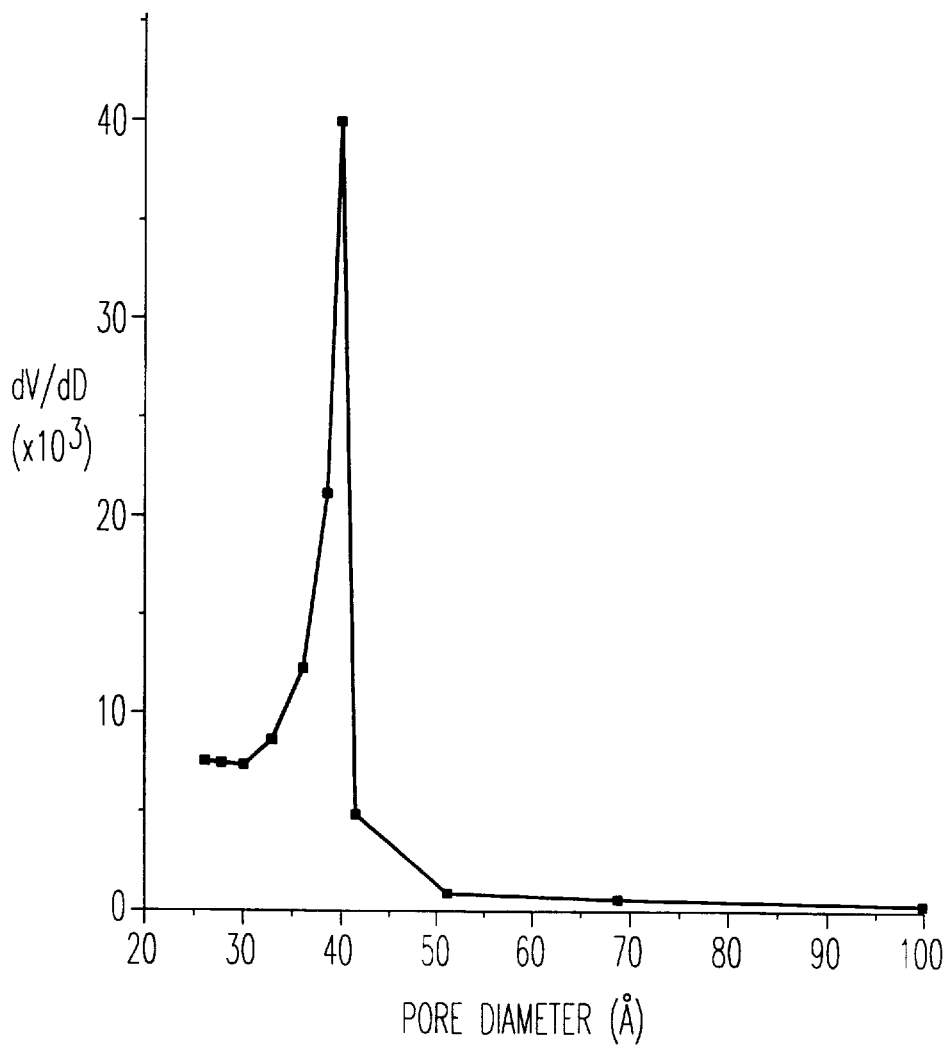

From the X-ray diffraction spectrum of the powders, shown in FIG. 4, an interstratum distance of 9.6 Å can be deduced. To determine the molar ratio diphosphonic acid/phosphorous acid in the solid, the nuclear magnetic resonance technique at $^{31}P$ is used. About 20 mg of solid are dissolved in a few drops of concentrated hydrofluoric acid, added to 1 ml of deuterated dimethylsulfoxide (DMSO-$d_6$, Carlo Erba RPE) and analyzed with a Bruker AC200 spectrometre. The molar ratio, which can be calculated from FIG. 5, is equal to 0.87:1. To obtain the porosity characteristics, the solid is first degassed at a temperature of 150° C. and at a pressure of 5×10⁻³ mmHg for 6 hours. A measurement of the surface area is then carried out by adsorption of nitrogen using the Carlo Erba instrument Sorptomatic 1800. The adsorption and desorption isotherm, shown in FIG. 6, shows a hysteresis loop which is typical of mesoporous solids. The mathematical treatment of the isotherm according to the B.E.T. theory provides a specific surface area of 390 m²/g and the pore distribution curve shows a single strong pick corresponding to pores with a diameter of 40 Å. From this curve it is calculated that 70% of the total porosity is between 30 and 50 Å in diameter (see FIG. 7).

EXAMPLE 2
Preparation of mesoporous zirconium phenylenediphosphonate-phosphite 1.03 g of 1,4-phenylenediphosphonic acid and 2.34 g of phosphorous acid are dissolved in 35 ml of water, kept in a plastic container. 2.15 g of $ZrOCl_2.8H_2O$ dissolved in 1.15 ml of concentrated HF and 4 ml of water are added to the limpid solution, maintained at 80° C. The solution thus obtained has the following composition: $[C_6H_4(PO_3H_2)_2]$= 0.1M, $[H_3PO_3]$=0.71M, $[Zr^{IV}]$=0.17M, $[HF]$=0.83M. The solution is maintained at 80° C. for 8 hours, ensuring that the volume remains constant. After this period the microcrystalline solid formed is separated from the solution by centrifugation, washed three times with about 50 ml of water and finally dried in an oven at 60° C. The solid zirconium diphosphonate-phosphite thus obtained is kept in a vacuum drier containing phosphoric anhydride.

The X-ray diffraction spectrum of the powders is similar to that of the previous example. The molar ratio diphosphonic acid/phosphorous acid in the solid, obtained as in the previous example, is 1.09:1. The measurement of the specific surface area by the adsorption of nitrogen gives a value of 295 m²/g and the pore distribution curve shows only one strong pick corresponding to pores having a diameter of 50 Å.

EXAMPLE 3
Functionalization of the mesoporous zirconium phenylenediphosphonate-phosphite with phenylenephosphonic-sulfonic acid.

1 g of the material obtained in example 1 is added to 58.5 ml of an 0.1M solution of phenylene-1phosphonic-3- sulfonic acid in dioxane at 90% in volume, i.e. consisting of 52.5 ml of dioxane, 6 ml of water and 1.5 g of phenylene-1-phosphonic-3-sulfonic acid.

The container is maintained under stirring at a temperature of 75° C. for 2 days. The solid is then separated by centrifugation, washed 3 times with 50 ml of dioxane, dried at 75° C. in an oven and conserved in a vacuum drier containing phosphoric anhydride. The X-ray spectrum of the powders does not show particular modifications with respect to the starting material.

Figure 8:
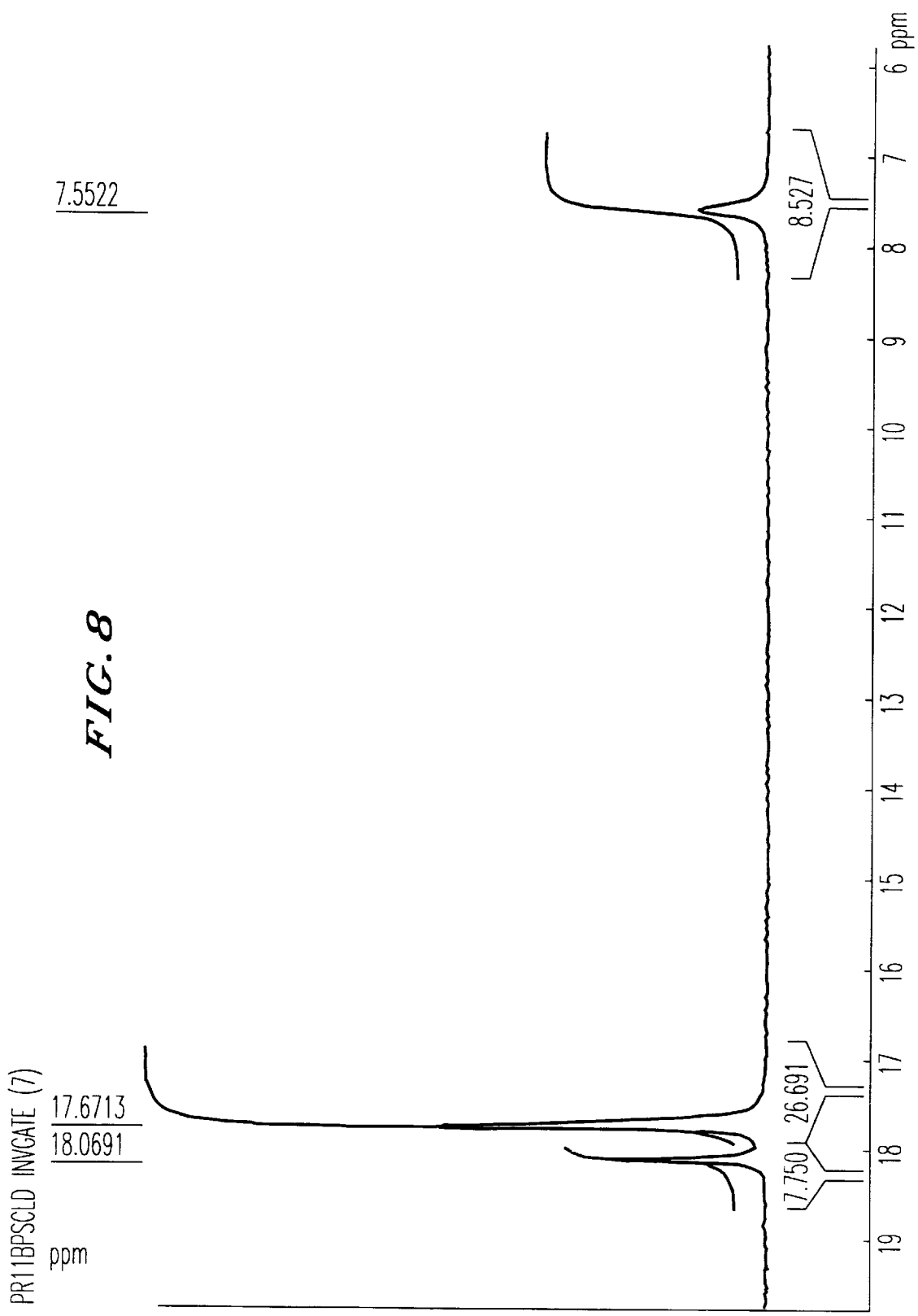

To determine the relative ratios between phenylene-diphosphonic acid, phenylenephosphonic-sulfonic acid and phosphorous acid in the solid, NMR analysis was used with Fourier transform at $^{31}P$, carried out under proton decoupling conditions by a sequence of impulses called "inverse gated decoupling", to ensure a quantitative measurement. These ratios are 1.20:0.56:1 (see FIG. 8).

The measurement of the surface area gives a value of 220 $m^2/g$, with a pore distribution curve centred on the diameter of 38 Å.

Figure 9:
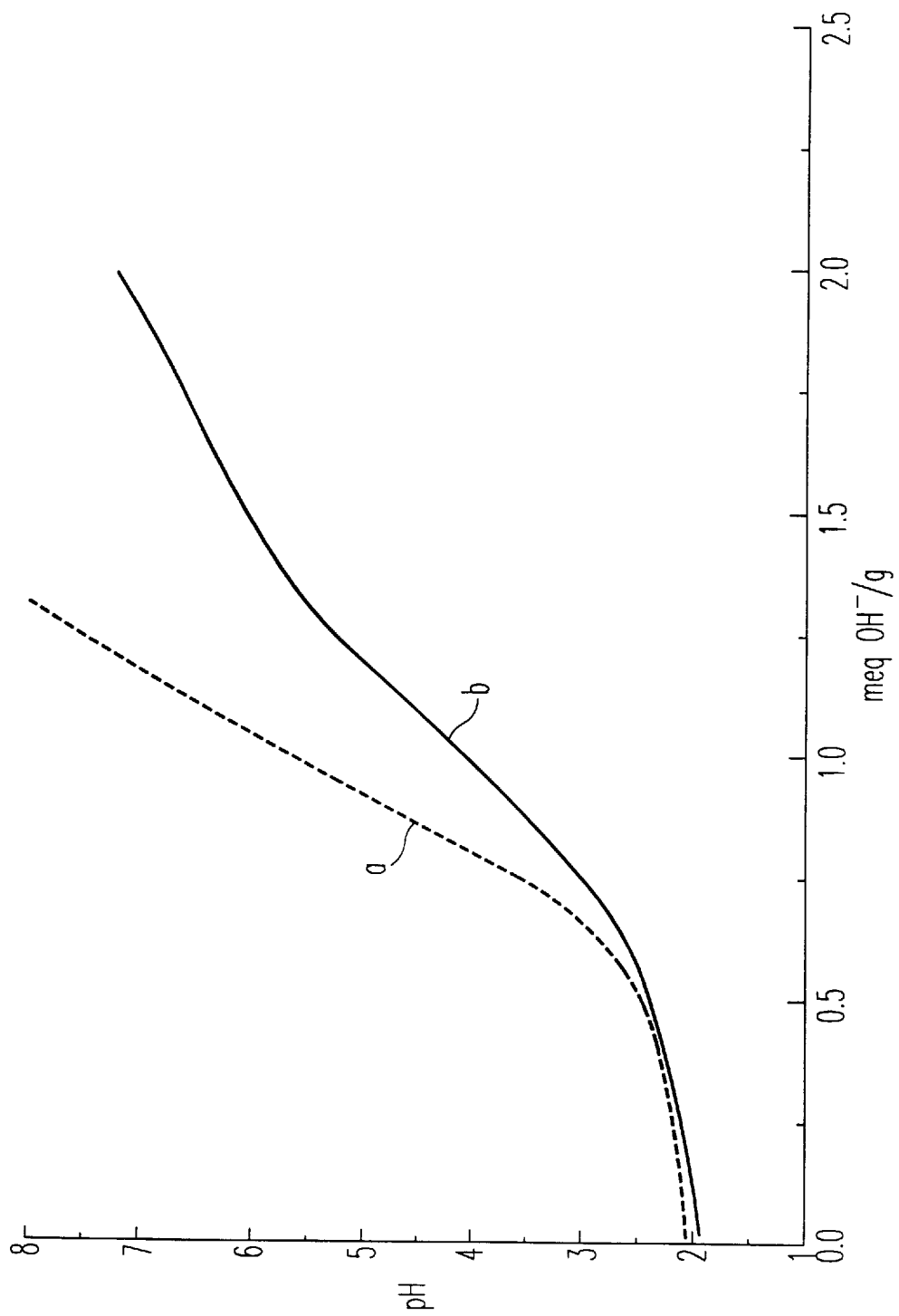

The increase in the acid groups and acid force of the solid after the topotactic exchange was shown by titration, with a solution of KOH 0.1M, of 0.300 g of a sample dispersed in 15 ml of a solution of KCl 1M. A Mettler DL40 automatic titrator was used for the purpose, with the "equilibrium" titration method. On comparing (see FIG. 9) the titration curves of the material before (curve a) and after the functionalization (curve b), both an increase in the cationic exchange capacity of the solid, due to the increase in the number of acid groups, and a lowering of the titration pH, which can be attributed to the increase in acid force due to the presence of the exchanged —$SO_3H$ groups, can be observed.

EXAMPLE 4

Functionalization of mesoporous zirconium Phenylenephosphonate-phosphite with phenylene-chlorosulfonyl-phosphonic acid.

10 g of the material obtained in example 1 are added to 585 ml of an 0.1M solution of phenylene-1-chlorosulfonyl-3-phosphonic acid in dioxane, i.e. consisting of 585 ml of dioxane and 15 g of phenylene-1-chlorosulfonyl-3-phosphonic acid.

The container is maintained under stirring at a temperature of 75° C. for 2 days. The solid is then separated by centrifugation, washed 3 times with 500 ml of dioxane. The dioxane is then eliminated by heating to 75° C. in an oven, the product is exposed to the air for 2–8 hours to allow the conversion of the —$SO^2Cl$ groups into —$SO_3H$ groups, and finally conserved in a vacuum drier containing phosphoric anhydride.

The X-ray spectrum of the powders does not show particular modifications with respect to the starting material.

The NMR analyses at $^{31}P$, carried out under the conditions described in example 3, provided the following relative molar ratios between phenylenediphosphonic acid, phenylenephosphonic-sulfonic acid and phosphorous acid in the solid: 1.57:0.92:1.

Figure 10:
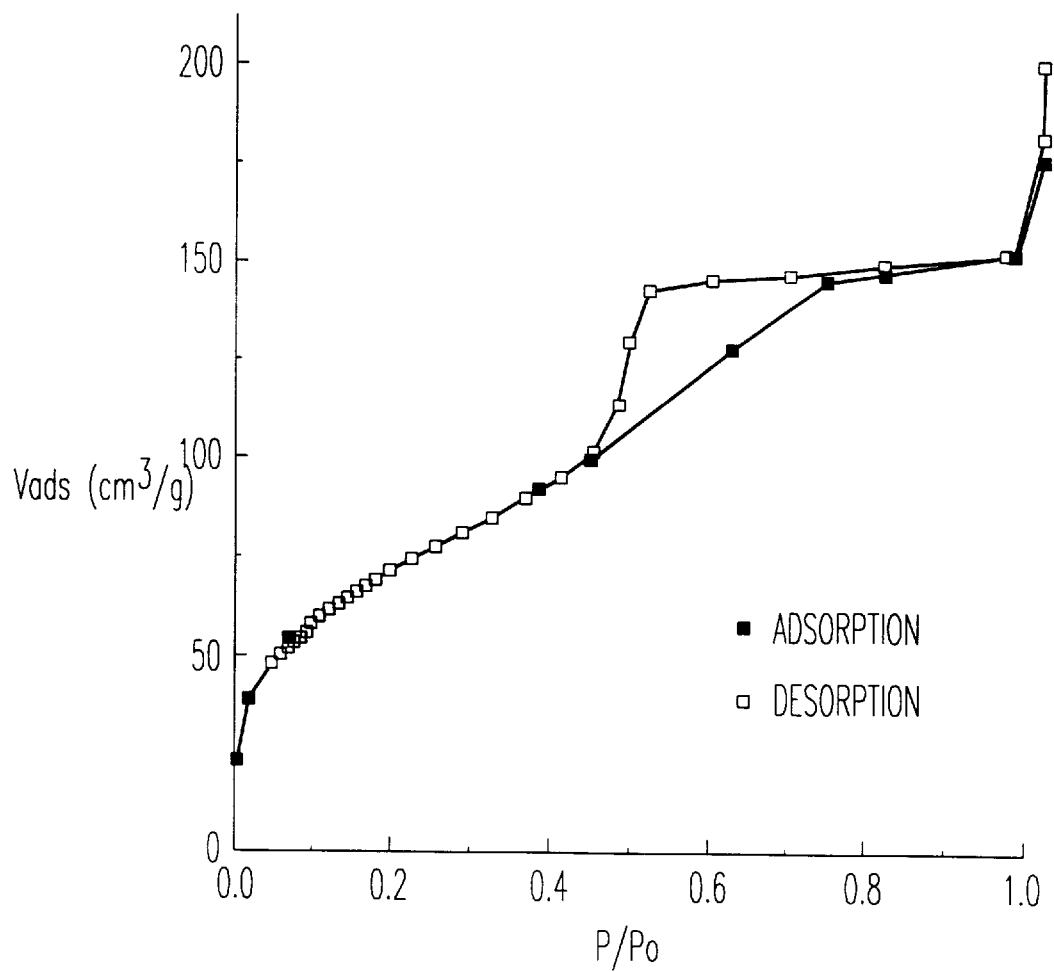
Figure 11:
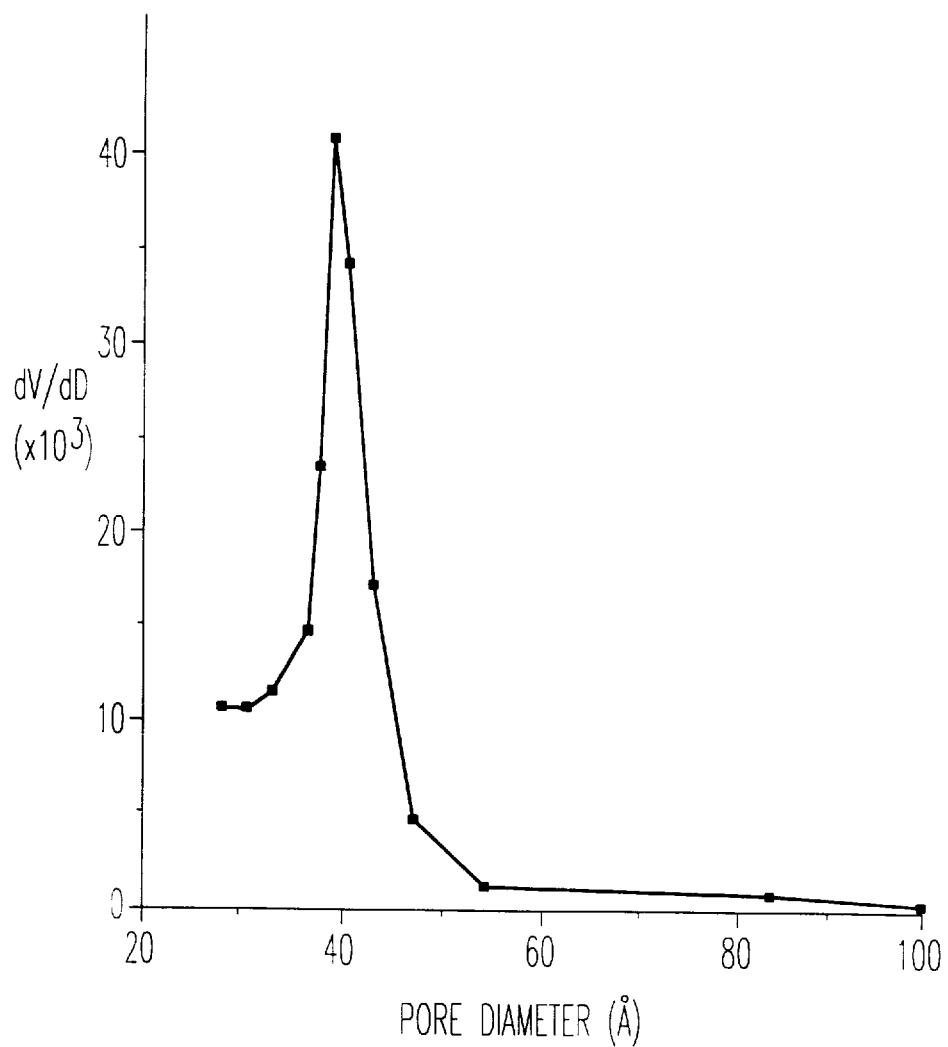

The measurement of the surface area gives a value of 260 $m^2/g$, with a pore distribution curve centred on the diameter of 38 Å. FIG. 10 shows the adsorption and desorption isotherm and FIG. 11 the pore distribution curve of the exchanged product.

Figure 12:
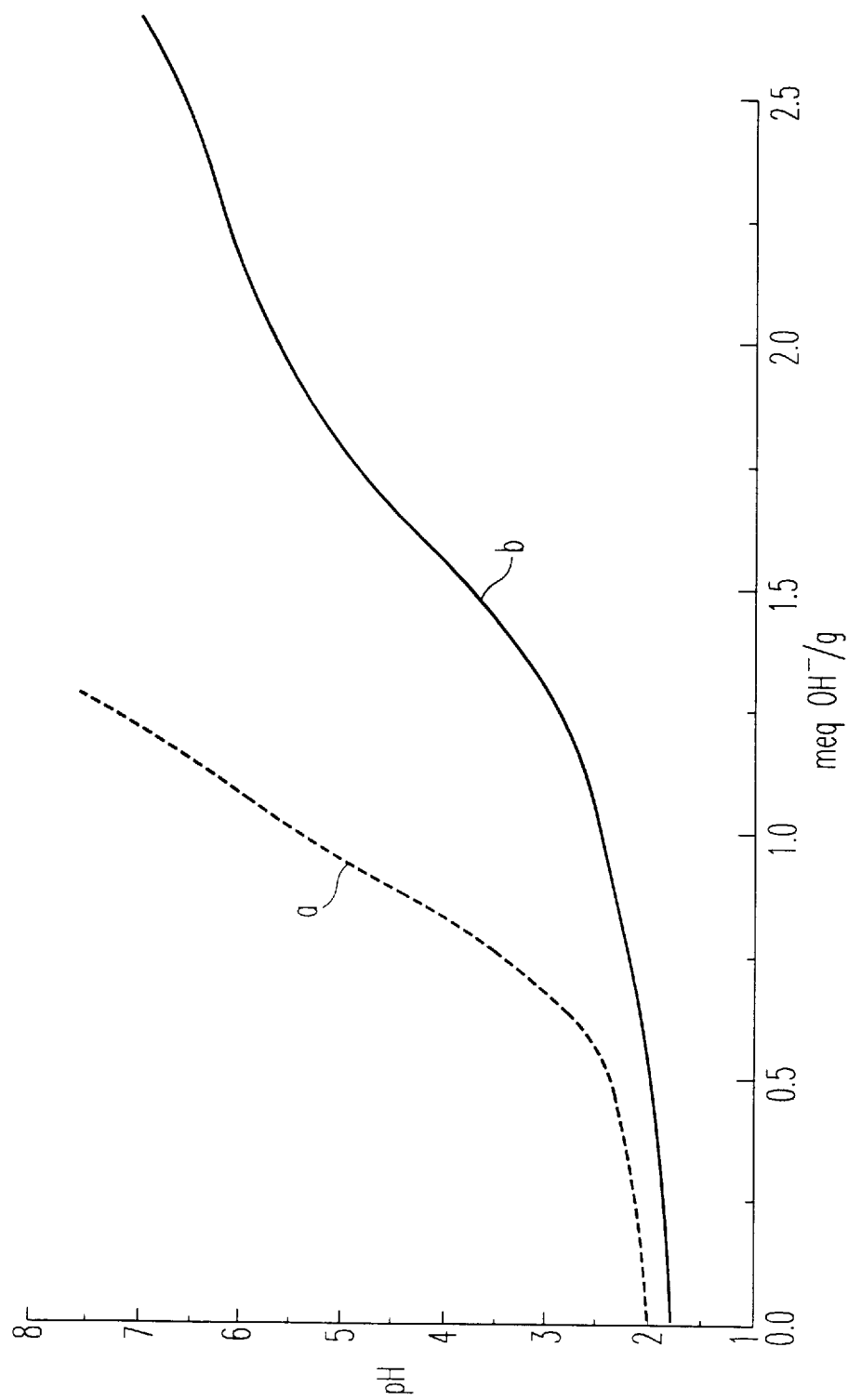

The increase in the acid groups and acid force of the solid after the topotactic exchange was shown by its titration under the conditions described in example 3. On comparing (see FIG. 12) the titration curves of the material before (curve a) and after the functionalization (curve b), both an increase in the cationic exchange capacity of the solid, due to the increase in the number of acid groups, and a lowering of the titration pH, which can be attributed to the increase in acid force due to the presence of the exchanged —$SO_3H$ groups, can be observed.

To ensure that the —$SO_2Cl$ groups of the functionalizing agent are completely converted into —$SO_3H$ groups, a portion of the sample was dispersed in an appropriate volume of a solution of KOH 0.1M, and maintained at boiling point for 3 hours to completely hydrolyze any chlorosulfonic groups still possibly present in the solid; the concentration of chloride ions present in this solution was then analyzed by ionic chromatography, using a Dionex 2000i/SP instrument. A negligible concentration of chloride ions is calculated from the chromatogram.

On comparing FIGS. 9b and 12b, it should be noted that the topotactic exchange with phenylene-chlorosulfonyl-phosphonic acid, relating to the present example, provides a better result than that obtained with the use of phenylenephosphonic-sulfonic acid relating to the previous example.

EXAMPLE 5

Functionalization of mesoporous zirconium phenylenediphosphonate-phosphite with phenylphosphonic acid and subsequent sulfonation.

10 g of the material obtained according to example 1 are put in contact with 350 ml of a 1M water solution of phenylphosphonic acid, i.e. consisting of 55.3 g of phenylphosphonic acid and 350 ml of water. The suspension is maintained at a temperature of 70° C. for three days under stirring, is then washed five times with 100 ml of water, dried in an oven and conserved in a vacuum drier containing phosphoric anhydride.

Figure 13:
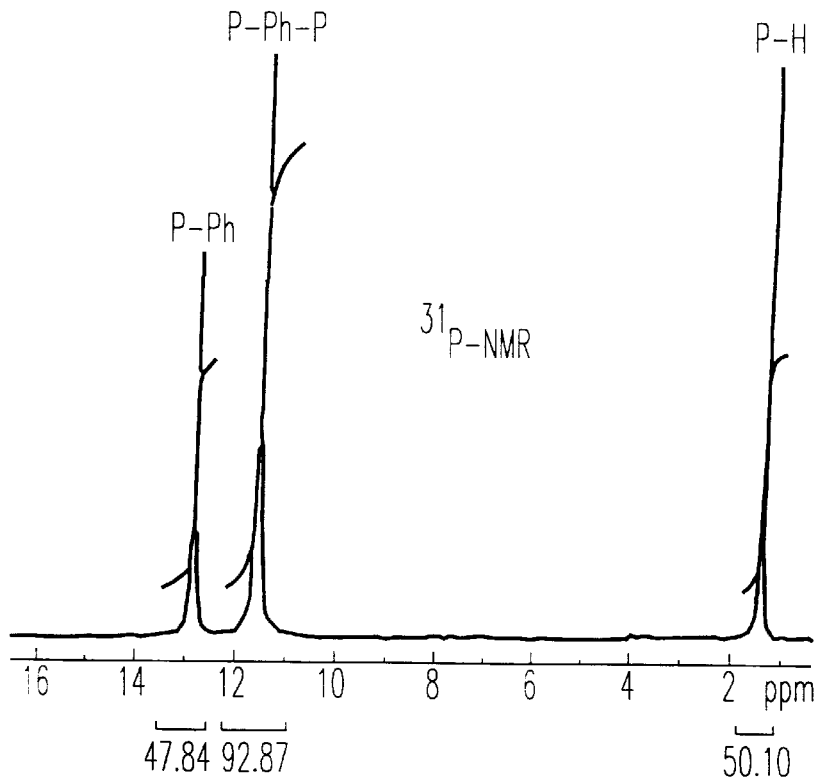

The $^{31}P$ NMR analysis provides the following molar ratios between phenylenediphosphonic acid, phenylphosphonic acid and phosphorous acid: 0.79:0.67:1 (see FIG. 13). The surface area measurement gives the value of 327 $m^2/g$ with a limited pore distribution centred on a diameter of 42 Å.

1 g of the product obtained as described above, is placed in a glass reactor equipped with magnetic stirring, cooling bath, internal thermometre with thermocouple, manometre and safety valve. The material is put in contact, at a temperature of −24° C. and under anhydrous conditions, with a solution at 10% (w/w) of $SO_3$ in $SO_2$. After 10 minutes of reaction the temperature is raised to 17° C. and left under these conditions for a further 30 minutes. The mixture is then heated to 33° C. and degassed, eliminating the unaltered sulfonating reagent. After repeated washings with nitrogen, the residue is recovered as a dark solid and purified by extraction in Soxhlet with tetrahydrofuran.

XRD analysis shows a profile which is basically unchanged with respect to the starting compound, with an interstratum distance of 9.6 Å.

Figure 14:
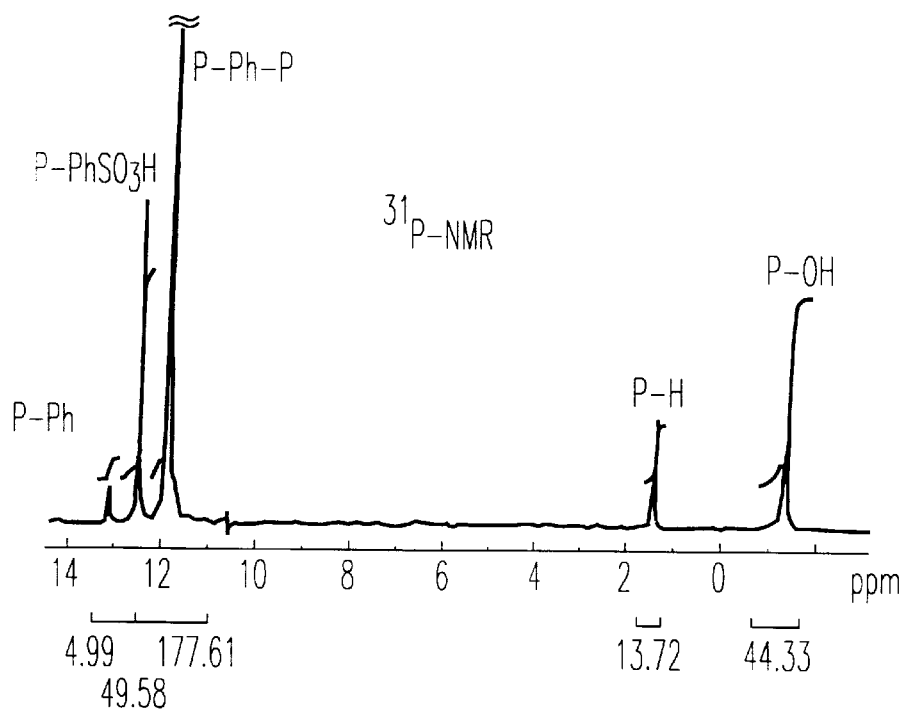

From the $^{31}P$ NMR analysis of the solid in a solution of HF—$H_2O$ (see FIG. 14) the following formula is obtained:

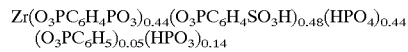

$Zr(O_3PC_6H_4PO_3)_{0.44}(O_3PC_6H_4SO_3H)_{0.48}(HPO_4)_{0.44}$
$(O_3PC_6H_5)_{0.05}(HPO_3)_{0.14}$

We claim:

1. A composition, comprising a diphosphonate of a tetravalent metal containing acid phosphite groups and diphosphonate groups anchored to the surface, having the formula:

$M((O_3P-R-PO_3)_{1-x-y}(HPO_3)_{2x}(O_3P-R-PO_3H_2)_{2y})$ wherein: M is a tetravalent metal, R is a bivalent organic radical, x varies from 0.3 to 0.6, and y varies from 0.05 to 0.3, the composition being in the form of a crystalline solid having the following characteristics:

i) a lamellar structure of the α-type with an interstratum distance of between 7.4 and 20 Å;

ii) a B.E.T. surface area of between 250 and 400 m²/g; and iii) a porosity in the range of mesopores, with at least 50% of the pores having a diameter greater than 30 Å and less than or equal to 50 Å.

2. The composition according to claim 1, wherein in the formula, M is a tetravalent metal selected from the group consisting of zirconium, titanium and tin.

3. The composition according to claim 2, wherein M is zirconium.

4. The composition according to claim 1, wherein in the formula, R is selected from the group consisting of aliphatic bivalent organic radicals containing from 2 to 10 carbon atoms in the molecule, aromatic radicals with from 1 to 2 non-condensed rings, and alkylaromatic radicals.

5. The composition according to claim 4, wherein the radical R is selected from the group consisting of —CH$_2$CH$_2$—, —CH$_2$—(CH$_2$)$_2$—CH$_2$—, —CH$_2$—(CH$_2$)$_4$—CH$_2$—, —C$_6$H$_4$—, —C$_6$H$_4$—C$_6$H$_4$—, and —CH$_2$—C$_6$C$_4$—C$_{6H4}$—CH$_2$—.

6. The composition according to claim 5, wherein R is selected from the group consisting of —C$_6$H$_4$— and —CH$_2$—(CH$_2$)$_2$—CH$_2$—.

7. A process for preparing the composition according to claim 1, which comprises reacting a diphosphonic acid R(PO$_3$H$_2$)$_2$, phosphorous acid H$_3$PO$_3$, and an oxychloride of a tetravalent metal MOCl$_2$, in a solvent selected from the group consisting of n-propanol and water containing hydrofluoric acid, according to the equation:

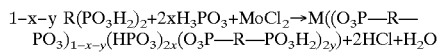

1-x-y R(PO$_3$H$_2$)$_2$+2xH$_3$PO$_3$+MoCl$_2$→M((O$_3$P—R—PO$_3$)$_{1-x-y}$(HPO$_3$)$_{2x}$(O$_3$P—R—PO$_3$H$_2$)$_{2y}$)+2HCl+H$_2$O wherein: M is a tetravalent metal, R is a bivalent organic radical.

x varies from 0.3 to 0.6, and y varies from 0.05 to 0.3.

8. The process according to claim 7, wherein the molar ratio between the diphosphonic acid and the phosphorous acid is between 1/2 and 1/20.

9. The process according to claim 7, wherein the molar ratio between the hydrofluoric acid and the tetravalent metal is between 5/1 and 30/1.

10. The process according to claim 7, wherein the molar ratio between the diphosphonic acid and the tetravalent metal is between 0.5 and 2.

11. The process according to claim 7, wherein the operating temperature is between about 10° and 130° C. and the time between about 1 and 100 hours.

12. The process according to claim 7, wherein the diphosphonic acid is selected from the group consisting of 1,4-benzene diphosphonic acid and 1,4-butane diphosphonic acid.

13. The process according to claim 7, wherein the oxychloride of the tetravalent metal is selected from the group consisting of zirconyl octahydrate ZrOCl$_2$.8H$_2$O and zirconyl chloride monohydrate ZrOCl$_2$H$_2$O.

14. A solid acid catalyst based on a diphosphonate-phosphite of a tetravalent metal which is obtained by a process, which comprises contacting a diphosphonate-phosphite of a tetravalent metal having the formula:

M((O$_3$P—R—PO$_3$)$_{1-x-y}$(HPO$_3$)$_{2x}$(O$_3$P—R—PO$_3$H$_2$)$_{2y}$)

wherein: M is a tetravalent metal,

R is a bivalent organic radical, x varies from 0.3 to 0.6 and y varies from 0.05 to 0.3.

having a lamellar structure of the α-type with an interstratum distance of between 7.4 and 20 Å, a B.E.T. surface area of between 250 and 400 m²/g, and a porosity in the range of mesopores, with at least 50% of the pores having a diameter greater than 30 Å and less than or equal to 50 Å, with a solution, in an aqueous or organic solvent or both, of i) a bifunctional phosphonic-sulfonic acid having the formula H$_2$O$_3$P—R'—SO$_2$X, wherein R' is a bivalent organic radical, and X is —OH or —Cl; or ii) an aryl phosphonic acid containing one or more aromatic rings;

for a time sufficient to at least partially exchange diphosphonate and phosphite surface groups of the diphosphonate-phosphite of the tetravalent metal with phosphonic-sulfonic groups or, respectively, with aryl phosphonic groups;

and, only in the case of the product exchanged with arylphosphonic acid, further subjecting the solid to sulfonation with a sulfonating agent.

15. The catalyst according to claim 14, wherein M is zirconium.

16. The catalyst according to claim 14, wherein R is selected from the group consisting of —CH$_2$CH$_2$—, —CH$_2$—(CH$_2$)$_2$—CH$_2$—, —CH$_2$—(CH$_2$)$_4$—CH$_2$—, —C$_6$H$_4$—, —C$_6$H$_4$—C$_6$H$_4$—, —CH$_2$—C$_6$H$_4$—CH$_2$—, and —CH$_2$—C$_6$H$_4$—C$_6$H$_4$—CH$_2$—.

17. The catalyst according to claim 14, wherein R is selected from the group consisting of —C$_6$H$_4$— and —CH$_2$—(CH$_2$)$_2$—CH$_2$—.

18. The catalyst according to claim 14, wherein the phosphonic-sulfonic acid is phenylene-1-chlorosulfonyl-3-phosphonic acid.

19. The catalyst according to claim 14, wherein the aryl phosphonic acid is selected from the group consisting of phenylphosphonic acid, biphenyl phosphonic acid, phenyl methyl phosphonic acid, diphenyl methyl phosphonic acid and triphenyl methyl phosphonic acid.

20. The catalyst according to claim 19, wherein the arlsulfonic acid is phenylphosphonic acid.

21. The catalyst according to claim 14, wherein an aqueous or organic solution or both of sulfonic-phosphonic acid or arylphosphonic acid is contacted with the solid compound (i) at a temperature of between about 20° and 100° C., for a time of between about 1 and 72 hours.

22. The catalyst according to claim 14, wherein a solution from 0.01M to 2M of sulfonic-phosphonic or arylphosphonic acid is used.

23. The catalyst according to claim 14, wherein the solvent is dioxane for the chlorosulfonyl-phosphonic acid, dioxane/water at 90% in volume of dioxane for the phosphonic-sulfonic acid, or water for the arylphosphonic acid.

24. The catalyst according to claim 14, wherein the sulfonating agent is sulfuric anhydride, and the sulfonation is carried out at a temperature of between about −30° C. and 50° C., for a time of between about 10 minutes and 20 hours.

25. A method of effecting molecular sieving, which comprises effecting the molecular sieving with the composition of claim 1.

26. A method of converting a hydrocarbon, which comprises contacting a hydrocarbon with the catalyst of claim 14, thereby converting said hydrocarbon.

* * * * *

UNITED STATES PATENT AND TRADEMARK OFFICE
CERTIFICATE OF CORRECTION

PATENT NO. : 5,892,080

DATED : April 6, 1999

INVENTOR(S): Giulio ALBERTI, et al.

It is certified that an error appears in the above-identified patent and that said Letters Patent is hereby corrected as shown below:

On the title page, item [75], the fourth inventor's last name should be:

--Zappelli--

Signed and Sealed this

Thirty-first Day of August, 1999

Attest:

Q. TODD DICKINSON

*Attesting Officer*

*Acting Commissioner of Patents and Trademarks*